United States Patent [19]

Herrick

[11] Patent Number: 4,605,398
[45] Date of Patent: Aug. 12, 1986

[54] DISPENSING DEVICE FOR CONTAINER HAVING FLUID TO BE CONTROLLABLY DISPENSED INTO AN EYE

[76] Inventor: Robert S. Herrick, 4134 N. Rosemead, Blvd. Rosemead, Calif. 91770

[21] Appl. No.: 602,358

[22] Filed: Apr. 20, 1984

[51] Int. Cl.[4] .............................................. A61N 1/00
[52] U.S. Cl. .................................... 604/300; 604/295; 604/302
[58] Field of Search ............... 604/300, 294, 295, 298, 604/301, 302, 176

[56] References Cited

U.S. PATENT DOCUMENTS

| | | | |
|---|---|---|---|
| 2,314,724 | 3/1943 | Marsan | 604/176 |
| 2,835,253 | 5/1958 | Borgeson | 604/176 |
| 3,016,898 | 1/1962 | Erwin | 604/301 |
| 3,279,466 | 10/1966 | Mings | 604/302 |
| 3,439,674 | 4/1969 | Lelicoff | 604/302 |
| 3,548,830 | 12/1970 | Goey | 604/176 |
| 3,872,866 | 3/1975 | Lelicoff | 604/302 |
| 3,945,381 | 3/1976 | Silver | 604/301 |
| 4,111,200 | 9/1978 | Sbarra et al. | 604/301 |
| 4,167,942 | 9/1979 | Brunelli | 604/301 |
| 4,173,226 | 11/1979 | Shell | 604/295 |

Primary Examiner—C. Fred Rosenbaum
Assistant Examiner—Mark Rooney
Attorney, Agent, or Firm—Daniel J. Meaney, Jr.

[57] ABSTRACT

A dispensing device adapted to be attached to a container having a fluid-dispensing opening through which fluid is to be controllably dispensed into an eye of a user wherein the dispensing device includes an attaching member which is adapted to be operatively coupled to the exterior of the container and positioned with the fluid-dispensing opening extending in a predetermined direction therefrom and a support member including a first end which is operatively coupled to the attaching member and a second opposed end which is located in a predetermined direction and which extends beyond the fluid-dispensing opening wherein the second opposed end terminates in a curvilinear, blade-like everting member having an outer ribbed edge which is adapted to be positioned against the outer skin below the lower eyelid and over a portion of the bone structure defining the eye socket of a user wherein the outer ribbed edge is capable of being urged against the bone structure with the skin therebetween to urge the skin in a downward direction from the eye which everts the lower eyelid from the eye of the user enabling drops of fluid to be directed into the eye in the absence of interference from the lower eyelid is shown.

22 Claims, 9 Drawing Figures

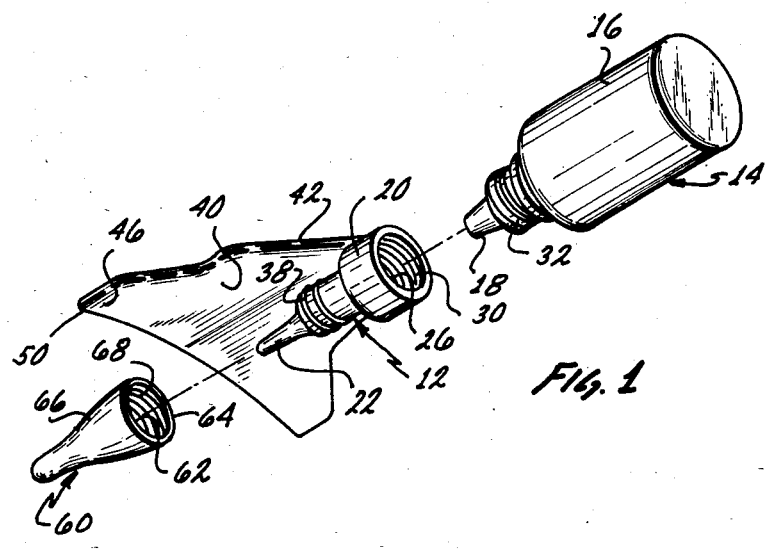
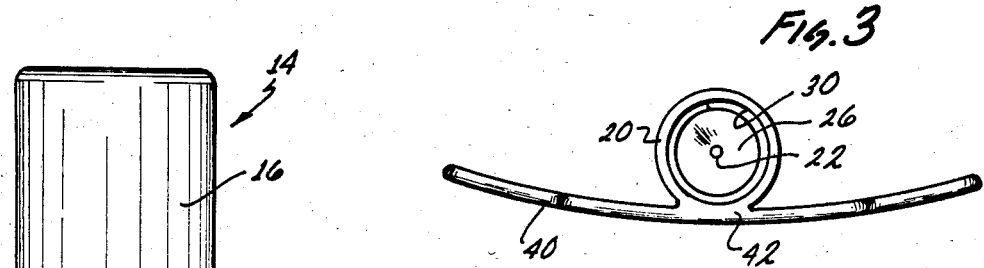
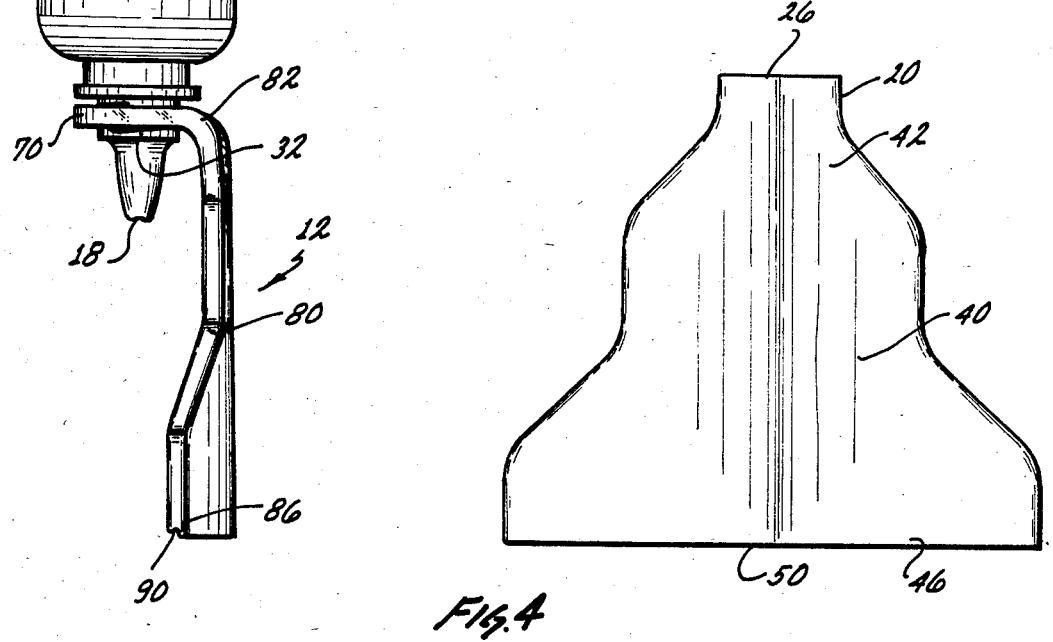

U.S. Patent  Aug. 12, 1986  Sheet 2 of 2  4,605,398
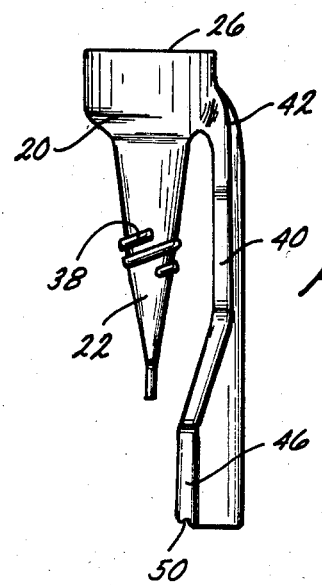
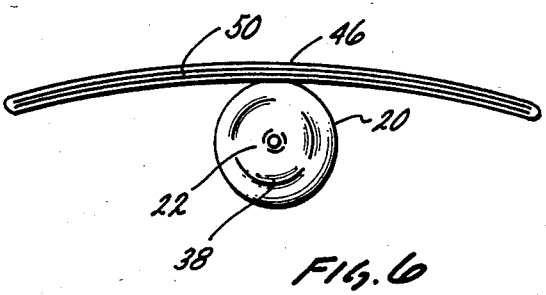
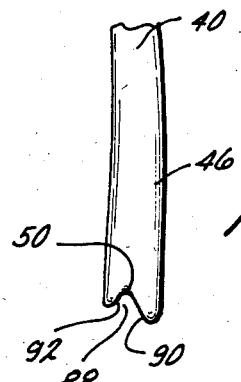
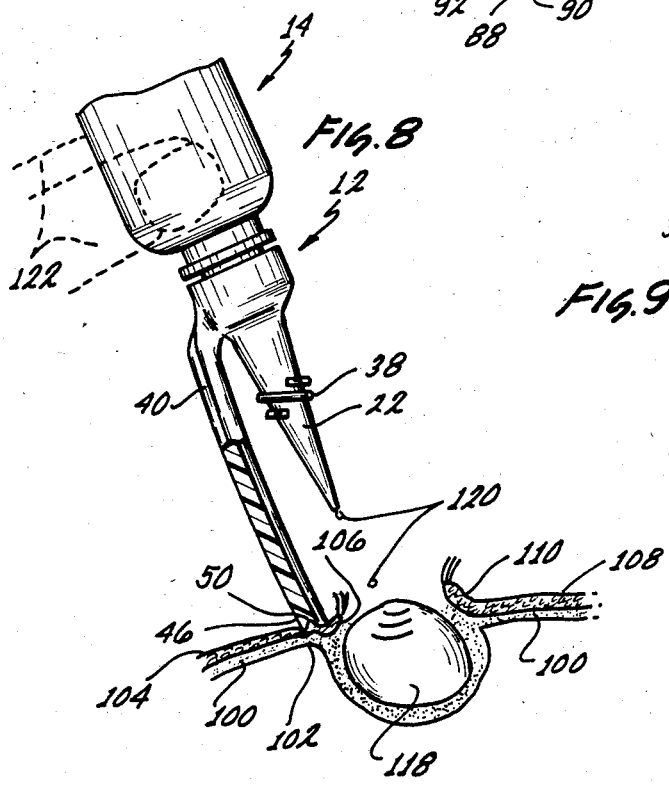
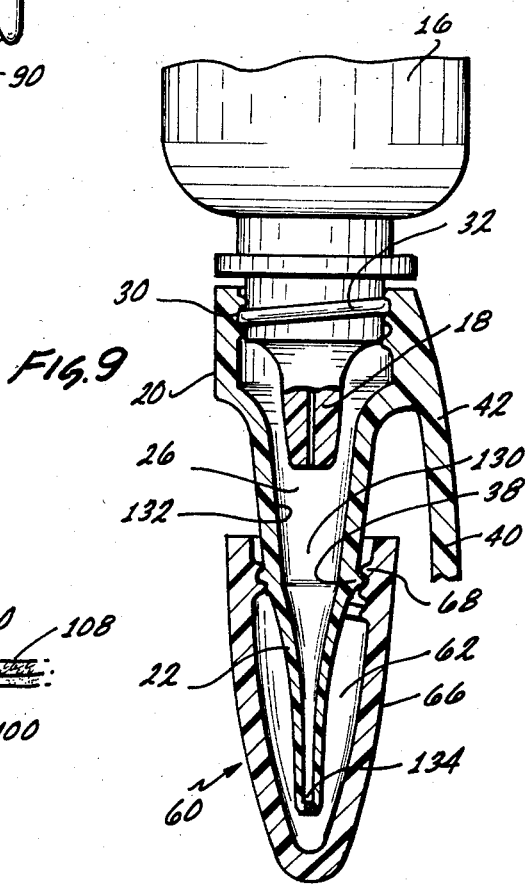

DISPENSING DEVICE FOR CONTAINER HAVING FLUID TO BE CONTROLLABLY DISPENSED INTO AN EYE

BACKGROUND OF THE INVENTION

1. Field of the Invention

This invention relates to a dispensing device adapted to be attached to a container having a fluid dispensing opening through which fluid is to be controllably dispensed into an eye through which fluid is to be controllably dispensed into an eye wherein the dispensing device includes a support guide means having a curvilinear, blade-like everting member in an outer ribbed edge which cooperates with the edge of the bone structure defining the eye socket for everting the eyelid enabling drops of fluid to be directed into the eye in the absence of interference from the lower eyelid and, more particularly, to a dispensing device having an elongated housing member which terminates in a fluid-dispensing tip for dispensing a controlled number of drops of fluid therefrom into an eye and a support member having a curvilinear, blade-like everting member to enable drops of fluid in a controlled amount to be directed into the eye in the absence of interference from the lower eyelid.

2. Description of the Prior Art

The use of an engaging device which is threaded onto the tapered neck of an eyewash container is known in the art. One such device disclosed in U.S. Pat. No. 3,872,866 includes an eyelid-engaging device which is adapted for mounting on the threaded or tapered neck of an eyewash container. The eyelid-engaging device has an aperture located at one end thereof which is adapted to be threaded onto the neck of the eyewash container so as to permit the free end thereof to permit eyewash to be dispensed drop-by-drop into an eye when the container is supported in an inverted position. When the container is supported in the dispensing position, the eyelid-engaging device firmly contacts the eyelid to maintain it in an open position as drops of the eyewash are directed into the eye.

U.S. Pat. No. 2,898,911 discloses an ophthalmic dispenser which is in the form of an eyecup which is adapted to be removably attached to the end of a container having fluid to be dispensed into the eye and wherein the nozzle is defined by a housing formed of relatively thin walls which terminates in an opening or outer lip which is adapted to be positioned over and enclose the eye so as to permit dispensing drop-by-drop dispensing of fluid into the eye.

U.S. Pat. No. 3,279,466 discloses an eyedrop aid for administering ophthalmic solution without excessive head tilting wherein the dispensing device includes a base having internal threads and an aperture which are adapted to be screwed onto the standard dispensing container which contains an eyedrop-dispensing nipple. The eyedrop aid is positioned onto the container such that the eyedrop-dispensing nipple extends through the aperture and is adapted to direct fluid onto the eye. The eyedrop aid includes an outer eyelid-engaging edge and a concave-convex surface so that the eyelid-engaging member is generally cup-shaped and will fit comfortably onto the eye. The eyedrop aid includes a web which extends outwardly of the base of the container and supports the cup-shaped eyelid-engaging surface in a spaced relation from the drop-dispensing nipple.

U.S. Pat. No. 3,439,674 discloses a liquid eyewash-dispensing device which includes an upper eyelid-engaging means. The eyelid-engaging means is in the form of an elongated rigid strip having pairs of arcuate claws which extend outwardly therefrom at one end thereof which are adapted to slidably and frictionably engage the exterior surface of a container and the other end of which is terminated in a elongated eyelid-engaging member which is adapted to engage and hold the upper eyelid of an eye in the open position. The eyelid-engaging member is positioned on the elongated strip at a distance which extends beyond the end of the neck of the container having the dispensing opening formed therein.

British Pat. No. 10,377 discloses apparatus which is adapted to apply a remedial agent to the eye in the form of a vapor or the like wherein the device utilizes a cup of a shape adapted to fit over the eye made of glass or a similar material. The cup includes a circular outer edge which is adapted to be positioned over and to enclose the eye. Means are operatively coupled to the eye cup to apply the vapor to the cup and onto the eye.

A number of dispensing devices which are adapted to utilize means for engaging the bridge or other portion of the nose are known in the art. Typical of such devices are those described in U.S. Pat. Nos. 4,134,403; 3,934,590; 3,521,636; 2,722,216; 2,676,592; and German Pat. No. 361,628. The design of an eyedrop bottle guide is disclosed in U.S. Pat. No. 249,709.

Devices for forming and/or controlling the formation of or dispensing of drops in a drop-by-drop relationship from a bottle is well known in the art. Typical of such devices are those disclosed in U.S. Pat. Nos. 2,619,262; 1,399,916; 783,688; French Pat. No. 1,263,954; British Pat. No. 1,208,686; and French Pat. No. 722,852.

In addition to the above, elongated nozzle members which are adapted for controlling the size and the dispensing of fluid in a drop-by-drop relationship are utilized in a number of adhesive dispensing devices, such as adhesives which essentially bond on contact. Also, it is known in the art to utilize elongated flexible dispensing tips in dispensing devices, for example, wood glue dispensers and the like.

SUMMARY OF THE PRESENT INVENTION

This invention relates to a novel, unique and improved control dispensing device which is adapted to be removably attached to a container having a fluid-dispensing opening through which drops of fluid are to be dispensed into the eye of a user. The dispensing device includes an elongated housing member having a hollowed-out central area which extends axially therethrough and which terminates at one end thereof in a container-receiving opening which is in axial alignment therewith and which is adapted to receive the fluid-dispensing opening and to support the container. The hollowed-out central area terminates at the other end thereof in a fluid-dispensing tip which is in axial alignment with the container-receiving opening. The fluid-dispensing tip has a selected length in a tapered passageway having two spaced opposed openings, one opening of which has a larger diameter than the other opening. The tapered passageway extends axially between the two opposed openings and is positioned with the larger diameter opening of the tapered passageway adjacent the fluid-dispensing opening in the container so as to receive fluid therefrom and which is adapted to direct the fluid received therefrom into and through the tapered passage to the other opening. The other opening dispenses a controlled number of drops of fluid therefrom. The support guide member includes a first end which is operatively coupled to the enlongated housing member with the fluid-dispensing tip extending in a predetermined direction from the fluid-dispensing tip and having a second opposed end which is located in the predetermined direction and at a distance greater than the selected length of the fluid-dispensing tip. The second opposed end terminates in a curvilinear, blade-like everting member having an outer ribbed edge which is adapted to be positioned against the outer skin below the lower eyelid and over a portion of the bone structure defining the eye socket of a user wherein the outer ribbed edge is capable of being urged against a bone structure with the skin therebetween to urge the skin in a downward direction which everts the lower eyelid from the eye of a user, enabling drops of fluid to be directed into the eye in the absence of interference from the lower eyelid.

None of the known prior art eye dispensing apparatus or attachments adapted to be operatilvely coupled to a container containing fluid to be dispensed into an eye suggests, teaches or utilizes a support guide means which includes a curvilinear, blade-like everting member having an outer ribbed edge which is adapted to be positioned against the outer skin below the lower eyelid and over a portion of the bone structure defining the eye socket of a user. Further, none of the known prior art devices suggests, teaches or discloses the use of a means for urging the outer ribbed edge of a curvilinear blade-like everting member against the bone structure defining the eye socket of a user with the skin therebetween being urged in a downward direction from the eye which everts the lower eyelid from the eye of a user enabling drops of fluid to be directed into the eye in the absence of interference from the lower eyelid.

U.S. Pat. No. 3,872,866 discloses a device having a support which terminates in a transverse eyelid-engaging member which is adapted to be positioned directly below the lower eyelid and above the edge of the bone structure defining the socket of an eye. The transverse eyelid engaging member in U.S. Pat. No. 3,872,866 functions to engage the eyelid to hold it in an open position by urging the skin immediately under the eyelid against the eyeball to prevent closure of the lower eyelid. Certain of the other devices in the art enclose the eye and perform the function of providing a dispensing platform such that the drops dispense from the container-dispensing nozzle are directed, by gravity, onto the eye. The device disclosed in U.S. Pat. No. 3,439,674 engages the upper eyelid and functions by holding the eyelid in an open position to prevent closure thereof.

The known prior art devices which utilize a support means which is positioned contiguous a portion of the nose principally operates to provide a steadying and positioning means of the dispenser relative to the eye preparatory to dispensing fluid therefrom into an eye.

The present invention overcomes certain of the disadvantages of the known prior art devices. One advantage of the present invention is that the dispensing device provides for safe use in dispensing of eye drops by a user self-administering fluid to an eye.

A further advantage of the present invention is that the dispensing device permits the predictable application of each drop directly to the eye of a user.

A yet further advantage of the present invention is that the apparatus prevents lid closure during application of the drops of fluid from a container operatively coupled to the dispensing device.

A yet further advantage of the present invention is that the dispensing device prevents the flexible dispensing tip from engaging the eye or eye surfaces and eliminates contamination which would otherwise occur if such contact was made.

A yet further advantage of the present invention is that the number and volume of drops applied to an eye can be controlled so as to decrease the systemic effects of the medication by the use of a flexible tip member which functions as a microdropper to control the number of drops applied to the eye of a user.

A yet further advantage of the present invention is that a conventional eye container having a dispensing nozzle and a threaded exterior surface which is adapted to receive and support an enclosing cap thereon can, upon removal of the cap, have the dispensing device threaded thereon which includes a fluid-dispensing opening for receiving the fluid-dispensing opening of the container and which includes a elongated flexible tip which functions as a microdropper for precisely controlling the size and quantity of drops to be dispensed drop-by-drop into the eye of a user.

A yet further advantage of the present invention is that medication fluid for an eye is extremely expensive; and, by use of the dispensing device of the present invention, the precise number of drops can be dispensed onto the eye of a user, thereby preventing excessive use of expensive medication, which is a extreme benefit both economically and medically to a user.

A yet further advantage of the present invention is that the dispensing device minimizes the loss of medication. Specifically, the dispensing device eliminates the difficulty arising from a user's instilling medication into the eye due to the user's being unable to focus on the medication bottle because of its close proximity to the eye, and the inability of the user to so focus on the medication bottle results in the medication's being instilled onto the cheeks or lids rather than into the eye itself, resulting in loss of medication.

A yet further advantage of the present invention is that the support and guiding means in the form of a curvilinear, blade-like everting member minimizes the danger of a user's poking the eye with the pointed tip of the medication container.

A yet further advantage of the present invention is that the design of the dispensing device allows for one-handed instillation of eye medication by a user into the eye.

A yet further advantage of the present invention is that the dispensing device permits instillation of eye solutions into the eye without disturbance of eye makeup and without involving manipulation of the upper eyelid. The ability to instill solutions into an eye without manipulation of the upper eyelid may be required due to some types of eye surgery and plastic surgery.

A yet further advantage of the present invention is that the dispensing device is functionable to instill solutions into the eye even when the eyelids are swollen or irritated.

BRIEF DESCRIPTION OF THE DRAWING

These and other objects and advantages of the invention, taken with its various features and advantages, can be more easily understood from the following and more detailed description of the preferred embodiment taken in conjunction with the accompanying drawings wherein:

FIG. 1 is a perspective view of a container, a dispensing device and a cap adapted to be removably threaded onto a dispensing device;

FIG. 2 is a front elevational view of a standard medical container having a dispensing device formed of an attaching means adapted to be operationally coupled to a standard fluid-dispensing container having a fluid-dispensing opening and a support guides including a curvilinear, blade-like everting member having an outer ribbed edge;

FIG. 3 is a top plan view of the dispensing device illustrated in FIG. 1;

FIG. 4 is a front plan view of a dispensing device of the present invention illustrating the attaching means and support guide means;

FIG. 5 is a left side plan view of the dispensing device illustrated in FIG. 4;

FIG. 6 is a bottom plan view of the dispensing device of FIG. 4 showing the outer ribbed edge of the curvilinear, blade-like everting member which is capable of being urged against the bone structure of the socket of a user;

FIG. 7 is a partial end view of a curvilinear, blade-like everting member illustrating the construction of the outer ribbed edge;

FIG. 8 is a pictorial representation of a dispensing device of the present invention operatively attached to a container wherein the dispensing device supports the flexible dispensing tip above the eye for dispensing fluid therein; and FIG. 9 is a pictorial representation of an elongated housing member having a hollowed-out central area which terminates in a fluid-dispensing tip which is in axial alignment therewith and which includes a threaded member which is adapted to removably have a cap threaded thereon.

DESCRIPTION OF THE PREFERRED EMBODIMENT

FIG. 1 illustrates a dispensing device, generally designated as 12, which utilizes the teachings of the present invention. The dispensing device 12 is adapted to be attached to a container 14 having a vessel 16 which stores the fluid to be dispensed into the eye of a user and a fluid-dispensing opening or nipple 18 through which the fluid is to be controllably dispensed into an eye of a user.

In the preferred embodiment, the attaching means 12 is an elogated housing member 20 having a hollowed-out central area which extends axially through the housing member. The attaching means 12 illustrated in FIG. 1 includes means for defining a fluid-dispensing tip 22 having a selected length. The fluid-dispensing tip 22 is in the form of a microdropper design and is adapted to control the number of drops of fluid to be dispensed into the eye of a user. The elongated housing member hollowed-out central area 26 terminates one end thereof in a container receiving opening which is in axial alignment with the hollowed-out central area 26. The container receiving opening end of the hollowed-out central area 26 has a threaded section 30 which is adapted to be removably threaded onto a threaded throat portion 32 which defines the fluid-dispensing opening 18 of the container 14.

The dispensing device 12 further includes means for defining a threaded member 38 which is located on the exterior surface of the flexible dispensing tip 22.

In the embodiment illustrated in FIG. 1, the dispensing device further includes a support guide means 40, which includes means defining a first end 42 which is operatively coupled to the attaching means 12, and a second opposed end 46 which is located in the predetermined direction of the flexible tip portion 22 of the attachment means 12. The second end 46 extends beyond the fluid-dispensing opening which, in the preferred embodiment, is a flexible dispensing tip 22. The second opposed end 46 terminates in a curvilinear, blade-like everting member having an outer ribbed edge 50. The outer ribbed edge 50 is adapted to be positioned against the outer skin below the lower eyelid and over a portion of the bone structure defining the eye socket of a user, as illustrated in FIG. 8. The outer ribbed edge 50 is capable of being urged against the bone structure with the skin therebetween so as to urge the skin in a downward direction from the eye which everts the lower eyelid from the eye of a user enabling drops of fluid to be directed into the eye in the absence of interference from the lower eyelid.

FIG. 1 also illustrates that a cap, shown generally as cap 60, has an elongated hollowed-out cavity 62 which is formed generally in the shape of the flexible dispensing tip 22. The hollowed-out cavity 62 includes an opening 64 which is adapted to pass the flexible dispensing tip 22 therethrough into the elongated hollowed-out cavity 62. The cap wall 66 which defines the opening 64 has threads 68 formed on the inner portion thereof which are adapted to mate with the threaded member 38 on the exterior surface of the flexible dispensing tip 22. The cap 60 is adapted to be removably attached to the dispensing device 12. The dispensing device 12 illustrated in FIG. 1 is formed into an integral member which is adapted to be removably attached onto the container 14. In the preferred embodiment, the dispensing device is formed of a plastic material.

FIG. 2 illustrates another embodiment utilizing the teachings of the present invention which is adapted to be used with the container 14, which may be a standard medication container. Specifically, the dispensing device 12 includes an attaching means 70 which is adapted to be operatively coupled to the exterior of the container 14 and specifically to the threaded portion 32 of the container 14 which defines the fluid-dispensing opening 18. The attaching means 70 is operatively coupled relative to the container such that the fluid-dispensing opening 18 extends in a predetermined direction therefrom.

The dispensing device illustrated in the embodiment of FIG. 2 includes a support guide 80, which includes means for defining a first end 82 which is operative coupled to the attaching means 70, and a second opposed end 86 which is located in the predetermined direction of the fluid-dispensing opening 18 and which extends beyond the end thereof as illustrated in FIG. 2. The second opposed end 86 terminates in a curvilinear, blade-like everting member having an outer ribbed edge 90 which is adapted to be positioned against the outer skin below the lower eyelid and over a portion of the bone structure defining the eye socket of a user as described in connection with FIG. 8.

The embodiments of FIG. 1 and FIG. 2 illustrate a self-dispensing device for enabling a user to dispense fluid from a container 14 into an eye wherein the container 16 includes a fluid-dispensing opening 18 and a supporting and guide member 80 attached to the container 16 for positioning the container 16 ! in a dispensing position above the eye of the user, as illustrated in FIG. 8. The self-dispensing device is characterized by a user engaging end, identified as 46 in FIG. 1 and 86 in FIG. 2, which is located a predetermined distance and direction from the fluid-dispensing opening. In FIG. 1, the fluid-dispensing opening is the flexible tip member 22. In FIG. 2, the fluid-dispensing opening is the fluid-dispensing opening 18 of the container 14. In each embodiment, the user engaging end terminates in a curvilinear, blade-like everting member having an outer ribbed edge, as described above. The outer ribbed edge is adapted to be positioned against the outer skin and below the lower eyelid and over a portion of the bone structure defining the eye socket of a user. This relationship will be considered in greater detail in the discussion relating to FIG. 8.

FIGS. 3, 4, 5 and 6 illustrate the dispensing device 12 of the preferred embodiment, as illustrated in FIG. 1. The curvilinear blade 40 is operative attached at its first end 42 to the elongated housing member 20. The hollowed-out central area 26 includes a threaded container receiving opening 30 to permit the controlled dispensing device to be removably attached to a container.

FIG. 4 illustrates that the curvilinear, blade-like everting member can have a small dimension at the first end 42 at the point where the same is operatively coupled to the elongated housing member 20. The second end 46, which includes means for defining the outer ribbed edge 50, is curvilinear in shape and has a blade-like edge to contact the bone structure defining the eye socket of a user.

FIG. 5 illustrates in the side view the relationship between the elongated housing member 20, the flexible dispensing tip 22 and the curvilinear, blade-like everting member 40. The flexible dispensing tip 22 extends from the elongated housing 20 in a predetermined direction, and the flexible dispensing tip has a selected length. The second end 46 of the curvilinear, blade-like everting member 40 likewise extends in the same predetermined direction and extends beyond the end of the fluid-dispensing opening located at the end of the fluid-dispensing tip 22. Thus, the curvilinear blade-like everting member 40 positions the flexible dispensing tip 22 above the eye of a user while preventing the end of the flexible tip 22 from engaging or otherwise contacting the eye directly.

FIG. 6 illustrates that the outer ribbed edge 50 is located along the entire exterior portion of the curvilinear, blade-like everting member 40. In the preferred embodiment, the elongated housing member 20 is positioned symmetrically relative to the curvilinear, blade-like everting member 40.

FIG. 7 illustrates the structure of the second end 46 of the curvilinear, blade-like everting member 40 which defines the outer ribbed edge 50. The outer ribbed edge 50 includes a central recessed area 88 which terminates on one edge thereof in a raised protruding lip 90 and on the other opposed edge thereof in a lower protruding lip 92.

FIG. 8 illustrates diagrammatically the self-dispensing device being held by a user to dispense fluid from the container 14 into an eye. The container 14 has the dispensing device attached thereto wherein the dispensing device includes the flexible tip dispenser 22. The curvilinear, blade-like everting member 40 has its second end positioned against the outer skin 104 and below the lower eyelid 106 and over a portion of the bone structure 100 and specifically that part of the bone structure defining the edge of the eye socket 102 of a user. The outer ribbed edge 46 is illustrated as being urged against the bone structure 102 with the skin 104 therebetween being urged in a downward direction from the eye 118 which everts the lower eyelid 106 from the eye of a user, enabling drops of fluid 120 to be directed into the eye 118 in the absence of interference from the lower eyelid 106. The user would be required to maintain the upper eyelid 110, which forms part of the upper skin 108, in the open position. The combination of the self-dispensing device 12 and the container 14 is held in position by fingers 122 of a user.

FIG. 9 illustrates in greater detail the structure of the fluid-dispensing tip 22 and the relationship between the flexible dispensing tip 22 and the fluid-dispensing opening 18 of the container 16. Specifically, the elongated housing 20 has a hollowed-out central area 26 which terminates on one end thereof in the threaded container-receiving opening 30 which is in axial alignment with the hollowed-out central area 26. The other end the hollowed-out central area 26 terminates at the other end thereof in a fluid-dispensing tip 22. The fluid-dispensing tip is likewise in axial alignment with the container-receiving opening 30. The fluid-dispensing tip 22 has a selected length and a tapered passageway 130 having two spaced opposed openings 132 and 134. Opening 132 has a larger diameter than the other opening 134. The tapered passageway 130 extends axially between the openings 130 and 132 and is in axial alignment therewith with the larger diameter 132 being located adjacent or spaced from the fluid dispensing opening 18 of the container 16. The large opening 132 is adapted to receive fluid from the container 16 and to direct the fluid received therefrom through the tapered passageway 130 to the smaller diameter opening 134. The smaller diameter opening 134 is adapted to dispense a controlled number of drops of fluid from the flexible dispensing tip.

FIG. 9 illustrates that the dispensing device is adapted to cooperate with a cap 60 having a hollowed-out area 62 and an outer wall 66. The cap has an elongated hollowed-out cavity formed generally in the elongated shape of the flexible dispensing tip 22. The cap includes a threaded opening 68 which is adapted to pass the flexible dispensing tip 22 therethrough into the elongated hollowed-out cavity of the cap. The threads on the threaded opening 64 formed on the inner portion of the opening of the cap 66 are adapted to mate with the fitted member 38 on the exterior surface of the flexible dispensing tip 22.

In the preferred embodiment, the dispensing device 12 can be an integral member having the elongated housing member, the flexible dispensing tip and the curvilinear, blade-like everting member in the form of a integral member removably attached to a container of fluid to be dispensed into an eye. Typically, the fluid would be a medication. Certain of the medications to be dispensed into the eye are extremely expensive, and excessive use thereof is both expensive to the consumer and results in the consumer expending additional money on medication which would otherwise be unnecessary if the precise number of drops of fluid would be precisely measured and controlled for dispensing into the eye. Also, excessive use of medication may result in adverse effects to a user. In concept, once the medication container is emptied, the emptied container can be removed from the dispensing device and replaced with a fresh container containing a new supply of medication.

Also, it is envisioned that the dispensing device could be made integral with or in combination with a container containing fluid to be dispensed into the eye. In that event, the opening of the top of the container would still be deemed the fluid-dispensing opening for purposes of coacting or cooperating with the passage of fluid through the elongated housing and into the elongated tapered passageway of the fluid-dispensing tip. Further, the fluid-dispensing tip can be designed in the form of a microdropper so as to control the volume of a drop and the number of drops very precisely. In the preferred embodiment, the size of the drop that is to be dispensed into the eye would be in the order of a volume of 5 milliliters to 15 milliliters with a volume of about 10 milliliters of fluid being preferred.

Also, certain of the known containers for dispensing medication have an acceptable fluid-dispensing opening or a dispensing of fluid need not be controlled in terms of the number of drops. Thus, it is contemplated to be within the teachings of this invention to utilize a dispensing device which utilizes the curvilinear, blade-like everting member which is adapted to have the outer ribbed edge thereof positioned against the outer skin and below the lower eyelid and over a portion of the bone structure defining the eye socket of a user wherein the outer ribbed edge is capable of being urged against the bone structure with the skin therebetween to urge the skin in a downward direction from the eye which everts the lower eyelid from the eye of a user enabling drops of fluid to be directed into the eye in the absence of interference from the lower eyelid. The attaching means can be in the form of an annular-shaped member having an aperture which is adapted to be threaded on and/or mated with the threaded portion of a neck of a container which terminates in a fluid-dispensing opening. The curvilinear, blade-like everting member will extend in the same direction as that of the fluid-dispensing opening and extend beyond the fluid-dispensing opening such that the same is positioned above the eye during use of the dispensing device by a user in self-administering or dispensing fluid into the eye.

What is claimed is:

1. A dispensing device adapted to be attached to a container having a fluid-dispensing opening through which fluid is to be controllably dispensed into an eye of a user comprising attaching means adapted to be operatively coupled to the exterior of a said container and positioned with said fluid-dispensing opening extending in a predetermined direction therefrom; and support guide means including means defining a first end which is operatively coupled to said attaching means and a second opposed eyelid everting end which is located in said predetermined direction and which extends beyond the fluid-dispensing opening, said second opposed eyelid everting end terminating in a curvilinear, blade-like everting member having an outer ribbed edge eye socket bone engaging member having two ribs, one of which is higher than the other, and which is adapted to be positioned against the outer skin and below the lower eyelid and over a portion of the bone structure defining the eye socket of a user wherein the outer ribbed edge is capable of being urged against the bone structure with the skin therebetween to produce movement of the skin relative to the eye socket bone engaging member to evert the lower eyelid when said engaging member is positioned with the higher rib away from the eye and against the eye socket bone, said eyelid everting member urging the skin in a downward direction from the eye which everts the lower eyelid from the eye of a user, enabling drops of fluid to be directed into the eye in the absence of interference from the lower eyelid.

2. The dispensing device of claim 1 wherein said container has a threaded throat portion which terminates in a fluid-dispensing opening and wherein said attachment means includes sidewall means defining a container-receiving opening including a hollowed-out central area having a threaded section which is adapted to be removably threaded onto said threaded throat portion of a said container.

3. The dispensing device of claim 2 wherein said attachment means includes means for defining a fluid-dispensing tip having a selected length for controlling the number of drops of fluid to be dispensed into the eye of a user.

4. The dispensing device of claim 3 wherein said means defining said fluid-dispensing tip further includes means for defining a tapered passageway having two spaced opposed openings, one of which has a larger diameter than the other, said larger diameter opening being adapted to be positioned adjacent the fluid-dispensing opening in a said container so as to receive fluid therefrom and to direct a said fluid into and through said tapered passageway to the other smaller opening for dispensing a controlled number of drops of fluid therefrom.

5. The dispensing device of claim 4 wherein said attachment means and said support guide means are formed into an integral member adapted to be removably attached onto a said container.

6. The dispensing device of claim 4 wherein said means for defining a fluid-dispensing tip form fluid droplets, each having a volume of approximately 10 milliliters.

7. The dispensing device of claim 5 wherein the integral member is formed of plastic.

8. The dispensing device of claim 5 wherein the integral member is adapted to be threaded onto a said container.

9. The dispensing device of claim 8 wherein the depth of the hollowed-out central area is adapted to receive and enclose a fluid-dispensing opening of a said container.

10. In combination, a container having a fluid-dispensing opening through which fluid is to be controllably dispensed into an eye;

a dispensing device including an attaching member operatively coupled to the exterior of said container and positioned with said fluid-dispensing opening extending in a predetermined direction therefrom; and a support guide member including means defining a first end which is operatively coupled to said attaching member and a second opposed eyelid everting end which is located in said predetermined direction and which extends beyond the fluid-dispensing opening, said second opposed eyelid everting end terminating in a curvilinear, blade-like everting member having an outer ribbed edge eye socket bone engaging member having two ribs, one of which is higher than the other, and which is adapted to be positioned against the outer skin and below the lower eyelid and over a portion of the bone structure with the skin therebetween to produce relative movement of the lower eyelid relative to the eye socket bone engaging member to evert the lower eyelid when said engaging member is positioned with the higher rib away from the eye and against the eye socket bone, said eyelid everting member urging the skin in a bone, said eyelid everting member urging the skin in a downward direction from the eye which everts the lower eyelid from the eye of a user, enabling drops of fluid to be directed into the eye in the absence of interference from the lower eyelid.

11. The dispensing device of claim 10 wherein said container has a threaded throat portion which terminates in a fluid-dispensing opening and wherein said attachment member includes sidewall means defining a container-receiving opening including a hollowed-out central area having a threaded section which is adapted to be removably threaded onto said threaded throat portion of said container.

12. The dispensing device of claim 11 wherein said attachment member and said support guide member are formed into an integral member removably attached onto said container.

13. The dispensing device of claim 10 wherein said attachment member includes means for defining a fluid-dispensing tip which forms fluid droplets, each having a volume of approximately 10 milliliters.

14. The dispensing device of claim 11 wherein the integral member is formed of plastic.

15. A self-dispensing device for enabling a user to dispense fluid from a container into an eye wherein the container includes a fluid-dispensing opening and a supporting and guiding member attached thereto for positioning the container in a dispensing position above the eye of a user wherein said supporting and guiding member is characterized by a user-engaging end which is located in a predetermined distance and direction from the fluid-dispensing opening and which terminates in curvilinear, blade-like everting member having an outer ribbed edge eye socket bone engaging member having two ribs, one of which is higher than the other, and which is adapted to be positioned against the outer skin and below the lower eyelid and over a portion of the bone structure defining the eye socket of a user wherein the outer ribbed edge is capable of being urged against the bone structure with the skin therebetween to produce movement of the skin relative to the eye socket bone engaging member to evert the lower eyelid when said engaging member is positioned with the higher rib away from the eye and against the eye socket bone, said eyelid everting member urging the skin in a downward direction from the eye which everts the lower eyelid from the eye of a user, enabling drops of fluid to be directed into the eye in the absence of interference from the lower eyelid.

16. A controlled dispensing device adapted to be removably attached to a container having a fluid-dispensing opening through which drops of fluid are to be dispensed into an eye of a user, said dispensing device comprising an elongated housing member having a hollowed-out conetral area extending axially therethrough which terminates at one end thereof in a container-receiving opening which is in axial alignment therewith and which is adapted to receive a said fluid-dispensing opening and to support a said container, said hollowed-out central area terminating at the other end thereof in a fluid-dispensing tip which is in axial alignment with said container-receiving opening, said fluid-dispensing tip having a selected length and a tapered passageway having two spaced opposed openings, one opening of which has a larger diameter than the other, said tapered passageway extending axially therebetween and being positioned with the larger diameter opening of the tapered passageway adjacent said fluid-dispensing opening in a said container so as to receive fluid therefrom and which is adapted to direct a said fluid received therefrom into and through said tapered passage to said other opening for dispensing a controlled number of drops of fluid therefrom; and a support guide member having a first end which is operatively coupled to said elongated housing member with said fluid-dispensing tip extending in a predetermined direction therefrom and a second opposed eyelid everting end which terminates in a curvilinear, outer edge ribbed eye socket bone engaging member having two ribs, one of which is higher than the other, to produce movement of the skin relative to the eye socket bone engaging member to evert the lower eyelid when said engaging member is positioned with the higher rib away from the eye and against the eye socket bone, said eyelid everting member being located in said predetermined direction at a distance greater than the selected length of said fluid-dispensing tip, said second opposed end being adapted to be positioned against the outer skin and below the lower eyelid and over a portion of the bone structure defining the eye socket of a user wherein the outer ribbed edge is capable of being urged against the bone structure with the skin therebetween to produce relative movement of the lower eyelid relative to the eye socket bone engaging member to evert the lower eyelid when said engaging member is positioned with the higher rib away from the eye and against the eye socket bone, said eyelid everting member urging the skin in a downward direction which everts the lower eyelid from the eye of a user, enabing drops of fluid to be directed into the eye in the absence of interference from the lower eyelid.

17. The dispensing device of claim 16 wherein said container has a threaded throat portion which terminates in a fluid-dispensing opening and wherein said attachment means includes sidewall means defining a container-receiving opening including a hollowed-out central area having a threaded section which is adapted to be removably threaded onto said threaded throat portion of a said container.

18. The dispensing device of claim 17 wherein said elongated housing member and said support guide member are formed into an integral member adapted to be removably attached onto a said container.

19. The dispensing device of claim 16 wherein said fluid-dispensing tip forms fluid droplets, each having a volume of approximately 10 milliliters.

20. The dispensing device of claim 18 wherein the integral member is formed of plastic.

21. The dispensing device of claim 17 wherein said integral member includes means for defining a threaded member on the exterior surface of said flexible dispensing tip and further comprising a cap having an elongated hollowed-out cavity formed generally in the shape of said flexible dispensing tip and an opening adapted to pass the flexible dispensing tip therethrough into said elongated hollowed-out cavity and threads formed on the inner portion of said opening which are adapted to mate with the threaded member on said exterior surface of said flexible dispensing tip.

22. The dispensing device of claim 17 wherein said raised ribbed edge includes a central recessed area which terminates on an edge thereof in a raised protruding lip and on the other edge thereof in a lower protruding lip.

* * * * *